United States Patent [19]

Welch

[11] 4,170,625

[45] Oct. 9, 1979

[54] AUTOMATIC ANALYZER DEVICE FOR CARRYING OUT CHEMICAL-CLINICAL AND KINETIC-ENZYMATIC ANALYSES ON FLUIDS, PARTICULARLY BIOLOGICAL FLUIDS

[76] Inventor: Henry H. Welch, No. 437, Via Nomentana, 00162 Roma, Italy

[21] Appl. No.: 908,992

[22] Filed: May 24, 1978

[51] Int. Cl.² .......................... G01N 1/14; G01N 1/18
[52] U.S. Cl. ..................................... 422/64
[58] Field of Search ................ 23/230 R, 253 R, 259; 141/130; 422/64; 356/222, 206

[56] References Cited

U.S. PATENT DOCUMENTS

| | | | |
|---|---|---|---|
| 3,193,358 | 7/1965 | Baruch | 23/253 R |
| 3,594,129 | 7/1971 | Jones | 23/253 R |
| 3,764,268 | 10/1973 | Kosowsky et al. | 23/253 R |
| 3,912,456 | 10/1975 | Young | 23/253 R |

*Primary Examiner*—R. E. Serwin
*Attorney, Agent, or Firm*—Trexler, Wolters, Bushnell & Fosse, Ltd.

[57] ABSTRACT

Apparatus comprising in combination, an analytic circular stage rotatably mounted on a casing containing the whole apparatus, means to stepwise rotate said stage, a set of sample-carrying test tubes located in an annular array on said stage, a set of reaction test-tubes located concentrically and outside of said sample-carrying test tubes, aligned radially with said sample-carrying tubes so that two reaction test-tubes will coincide with each sample-carrying test tube, a first needle-carrying head located above said stage and destined to draw the sample and to add the reagents, and a second needle carrying head, located by side of the first cited head and destined to draw the liquid from the reaction tubes and to send it to the metering instruments.

14 Claims, 6 Drawing Figures

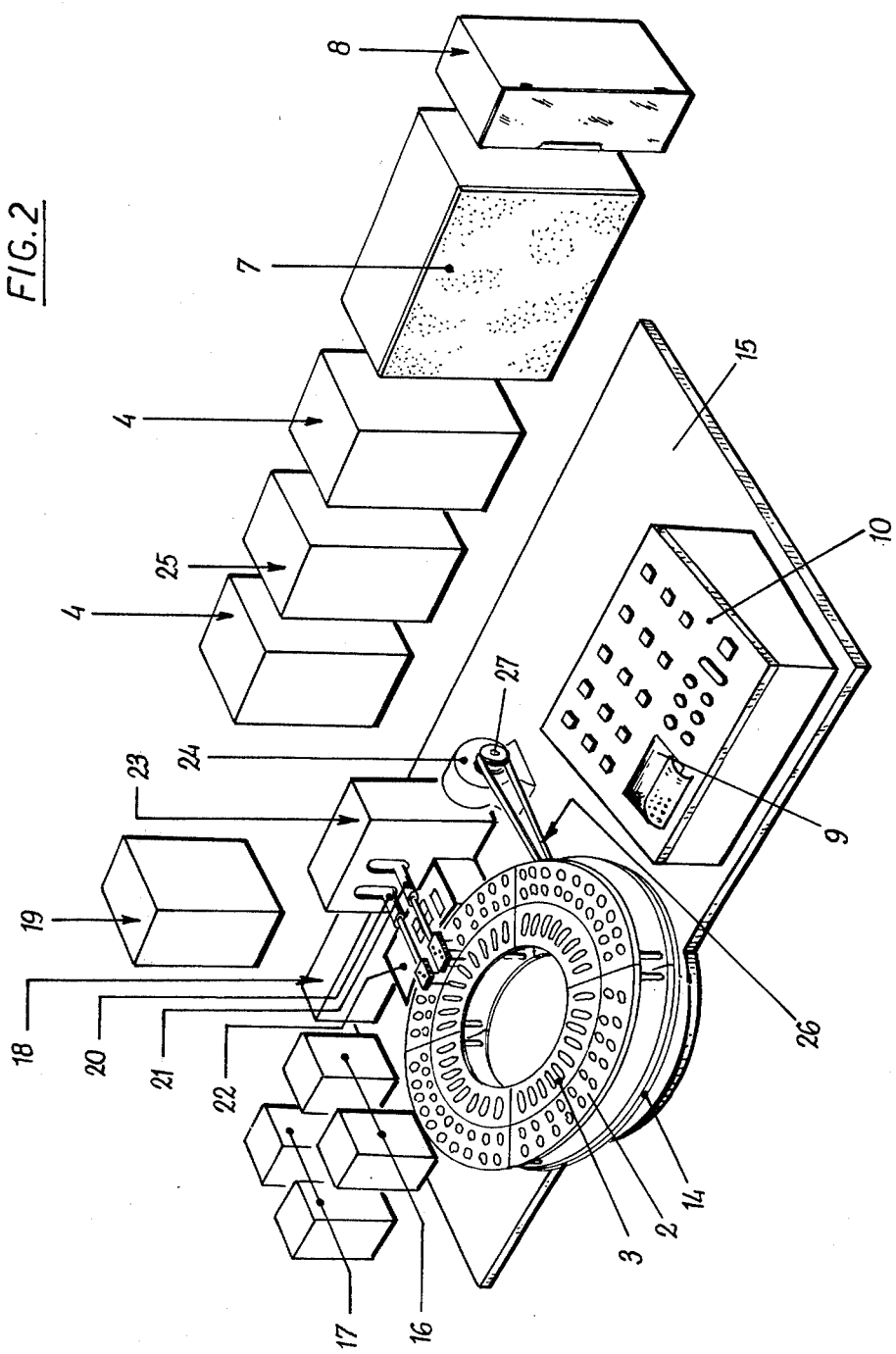

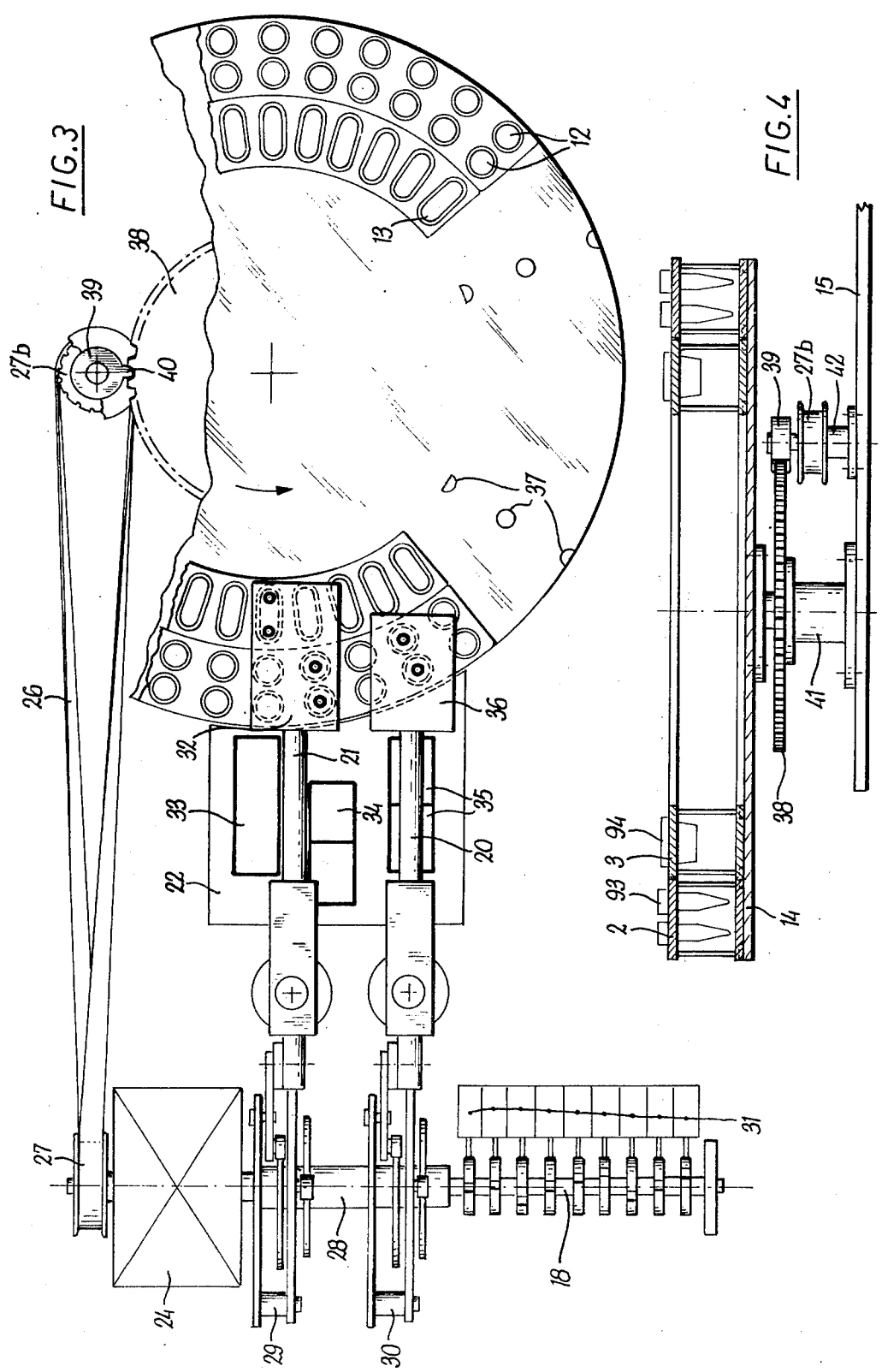

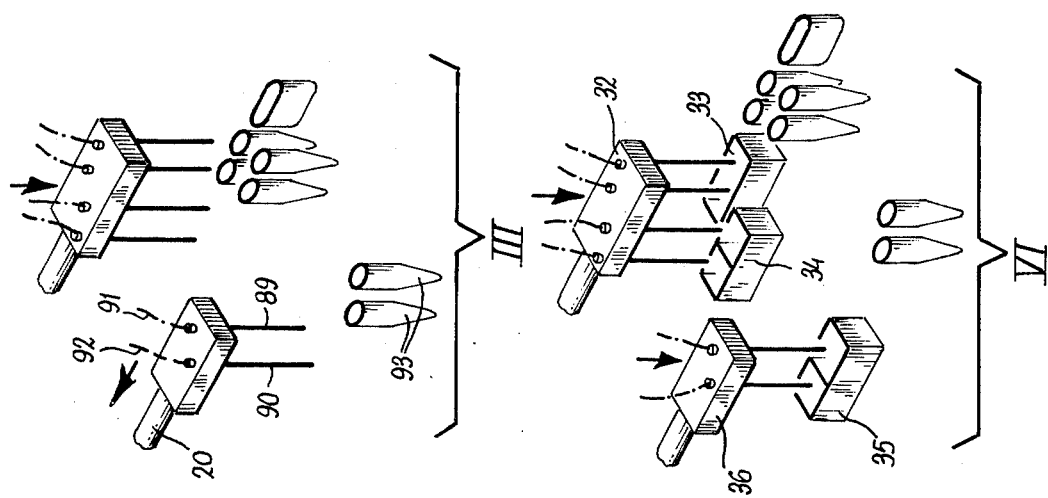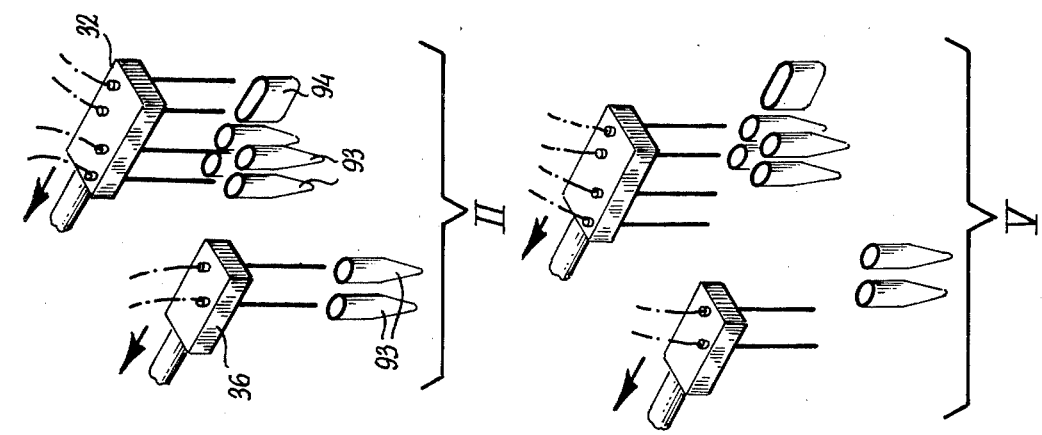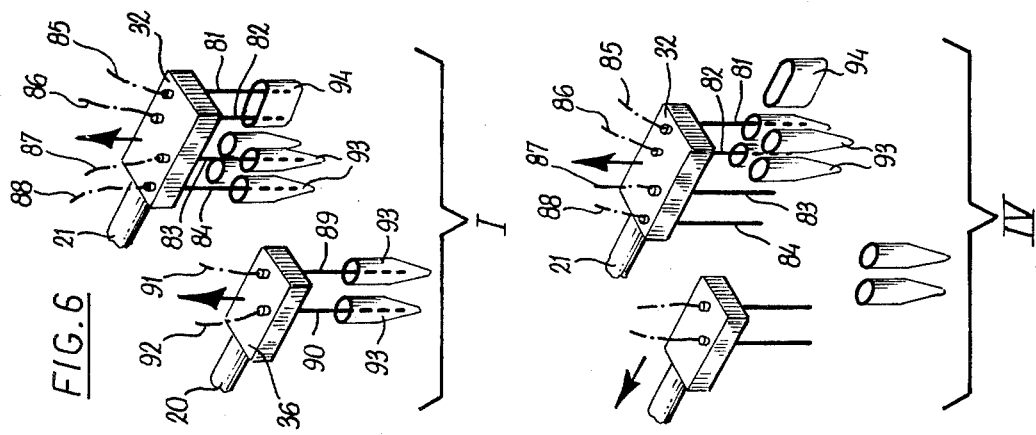
FIG.6

AUTOMATIC ANALYZER DEVICE FOR CARRYING OUT CHEMICAL-CLINICAL AND KINETIC-ENZYMATIC ANALYSES ON FLUIDS, PARTICULARLY BIOLOGICAL FLUIDS

The present invention relates to an apparatus allowing analyses to be carried out quickly and carefully on groups of liquid samples, particularly two types of analyses simultaneously, on the same sample.

More specifically, this invention relates to a completely automatic apparatus carrying out all analytic steps of the chemical-clinical and kinematic-enzymatic analyses using micro-amounts of both the sample and the reagent. The apparatus carries out automatically the drawing of the samples, drawing simultaneously either one or two amounts at the time, of the same sample, it adds reagents, it effects the incubation, and it transfers the liquid for metering into the photometer (s) (one or two) incorporated for the read out.

A suitably programmed computer processes the data and prints automatically one or two results, for the wanted concentrations.

The main purpose of the present invention is that of providing an automatic equipment capable of carrying out with a great precision and quickly a large number of analyses, one or two at the time, with minimum amounts of both the reagents and the sample.

The apparatus according to this invention offers to the analysis laboratories a quick and versatile system to render completely automatic the either routine or complex analyses, eliminating each possibility of human error, using minimum amounts of reagents, about 10 times less than the manual methods, obtaining thus a large financial saving. Also the apparatus can be operated by a non specialized staff, for carrying out analyses which can be committed at present only to highly qualified staff. The apparatus is entirely automatic, operated by an expressely programmed computer, allowing only the sample to be introduced in order to obtain the final result shown on a display screen and/or printed on paper.

According to this invention, an apparatus is provided comprising in combination, an analytic circular stage rotatably mounted on a casing containing the whole apparatus, means to stepwise rotate said stage, a set of sample-carrying test tubes located in an annular array on said stage, a set of reaction test-tubes located concentrically and outside of said sample-carrying test tubes, aligned radially with said sample-carrying tubes so that two reaction test-tubes will coincide with each sample-carrying test tube, a first needle-carrying head located above said stage and destined to draw the sample and to add the reagents, and a second needle carrying head, located by side of the first cited head and destined to draw the liquid from the reaction tubes and to send it to the metering instruments.

Said sample-carrying test tubes and the reaction tubes are inserted on supports having the shapes of circular sectors, removably mounted on said stage, so that groups of sample-carrying test tubes with the relative associated reaction test tubes can be quickly substituted, each time the group has overpassed the needle carrying heads.

Still according to this invention, the first head is provided with two pairs of needles, one of which dips into the sample carrying test tube, draws two micro-amounts of the sample itself, and deposits them into two different reaction tubes, while the second pair of needles enters the reagent into the reaction test tubes.

The second needle carrying head or transfer head is provided with a sole pair of needles which dip into the reaction tubes in order to draw the liquid and send it to the metering apparatus.

This invention will be now described with reference to the attached drawings showing by way of non limitative example one preferred embodiment of the invention itself.

In the drawings:

FIG. 1 is a perspective view of the apparatus according to this invention;

FIG. 2 diagrammatically shows the unit of the components, partially in exploded view;

FIG. 3 shows the control unit for the analytic stage and the needle-carrying heads, seen from top downwards;

FIG. 4 is a side elevational view corresponding to FIG. 3;

FIG. 6 diagrammatically sequentially shows the various operative stages of the two needle-carrying heads.

Figure 1:
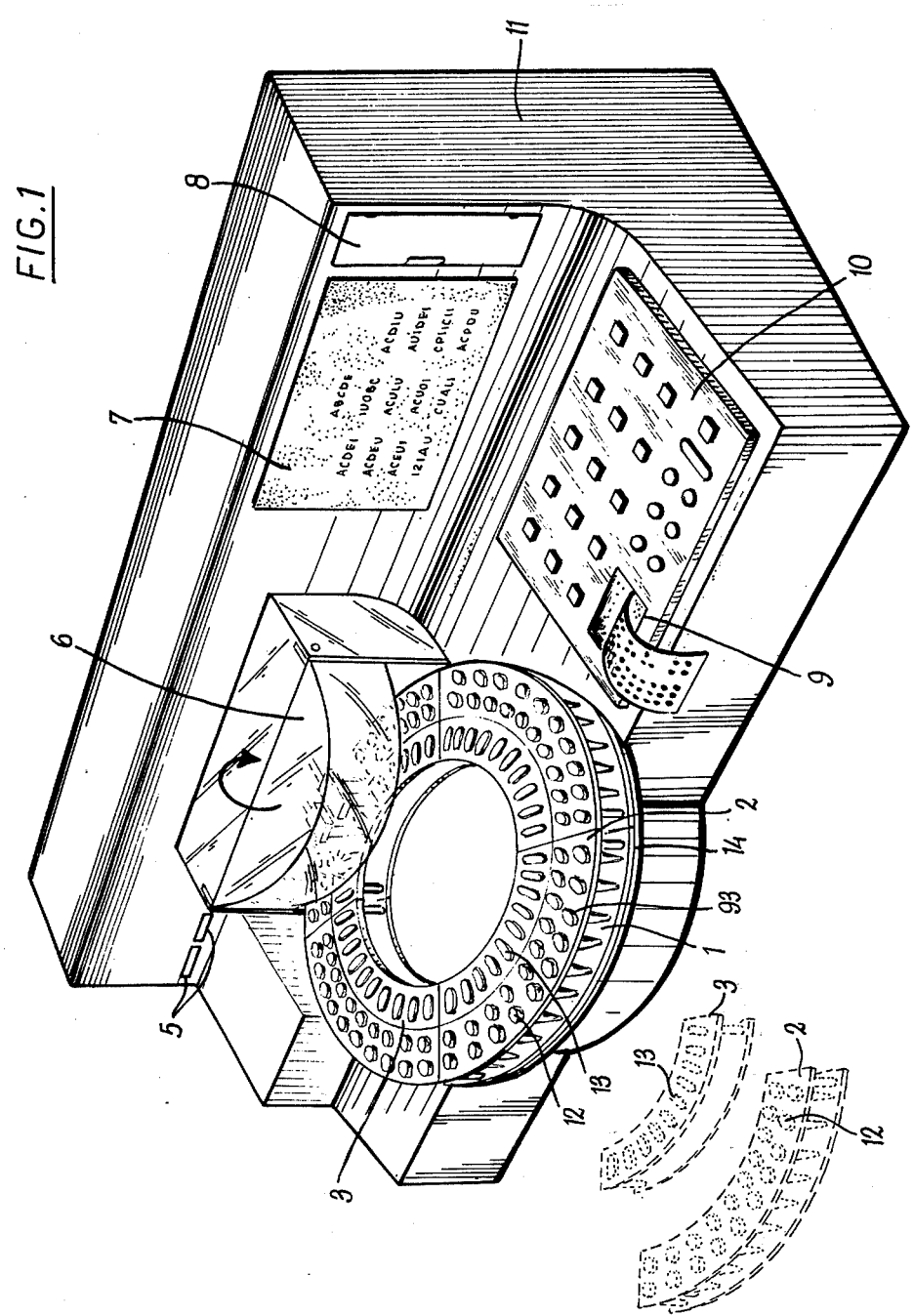

With reference to FIGS. 1 to 3, the apparatus includes a circular analytic stage 1 consisting of four equal sectors. Each sector 2 contains two rows of equal holes 12 destined to receive the test-tubes 93. Each sector 2 contains two rows each of ten or more holes. The sectors 2 rest on a support plate 14. Internally to said analytic stage 1 rests a sample carrying stage 3 having a circular shape, and it also consists of four sectors 3. Said analytic 2 and sample carrying 3 stages rest on the support plate 14 and are held and centered by the locating pegs 17. Within the casing 11 are incorporated all systems required to perform the operations as wanted. The apparatus includes also a protection cover 6 for the sampling system, a display 7 of the controls, a door recess 8 for the adjusting controls, a control board 10 for the computer and the printing of the data 9. The knobs 5 serve for adjusting the amount of sample which will be drawn.

The FIG. 2 shows all operative parts forming the analyzer, and precisely: two photometers 16 for metering the samples, two micro-drawing systems 17 for the transfer of the liquid for its metering, a double doser 19 which carefully doses the amounts of reagents necessary for the analyses (one or two at the time) a mechanical group 23 for the movement of the two arms, a block 22 provided with a thermostat containing recesses for the reagent and the washing liquid. The reference number 18 denotes a control cam system for three horizontal and vertical movements as described more in detail hereinafter. Also, two samplers 4 continuously and simultaneously adjustable, are provided and a support base 15 whereon are fixed the parts forming the apparatus.

The FIG. 3 shows the motor 24 which drives a shaft 28 whereon are mounted the arms 20 and 21, the cam system 18 for the checking signals and their respective micro-switches 31. On the same shaft 28 is mounted a pulley 27 which through the driving belt 26 drives a second pulley 27b which moves a cam 39 with a tooth 40 for driving the toothed wheel 38 which in turn moves the support plate 14 on which are located the sectors of the analytic stage 2 and the sectors of the sample carrying stage 3, through the locating pegs 37. The block 22 provided with thermostat contains the recess 33 for the sample washing liquid, two recesses containing reagent liquid, and two recesses 35 containing the washing liquid for the metering cup of the photometer.

The FIG. 4 shows the base of the apparatus 15 whereon is fixed the central support 41 supporting the toothed wheel 38 which is rotated by the cam 39 in turn operated by the driving wheel 27b. On the toothed wheel 38 is fixed the support plate 14 of the analytic stage 1 and the sectors 2 and 3 of the reaction test tubes 93 and of the sample carriers 94.

Figure 5:
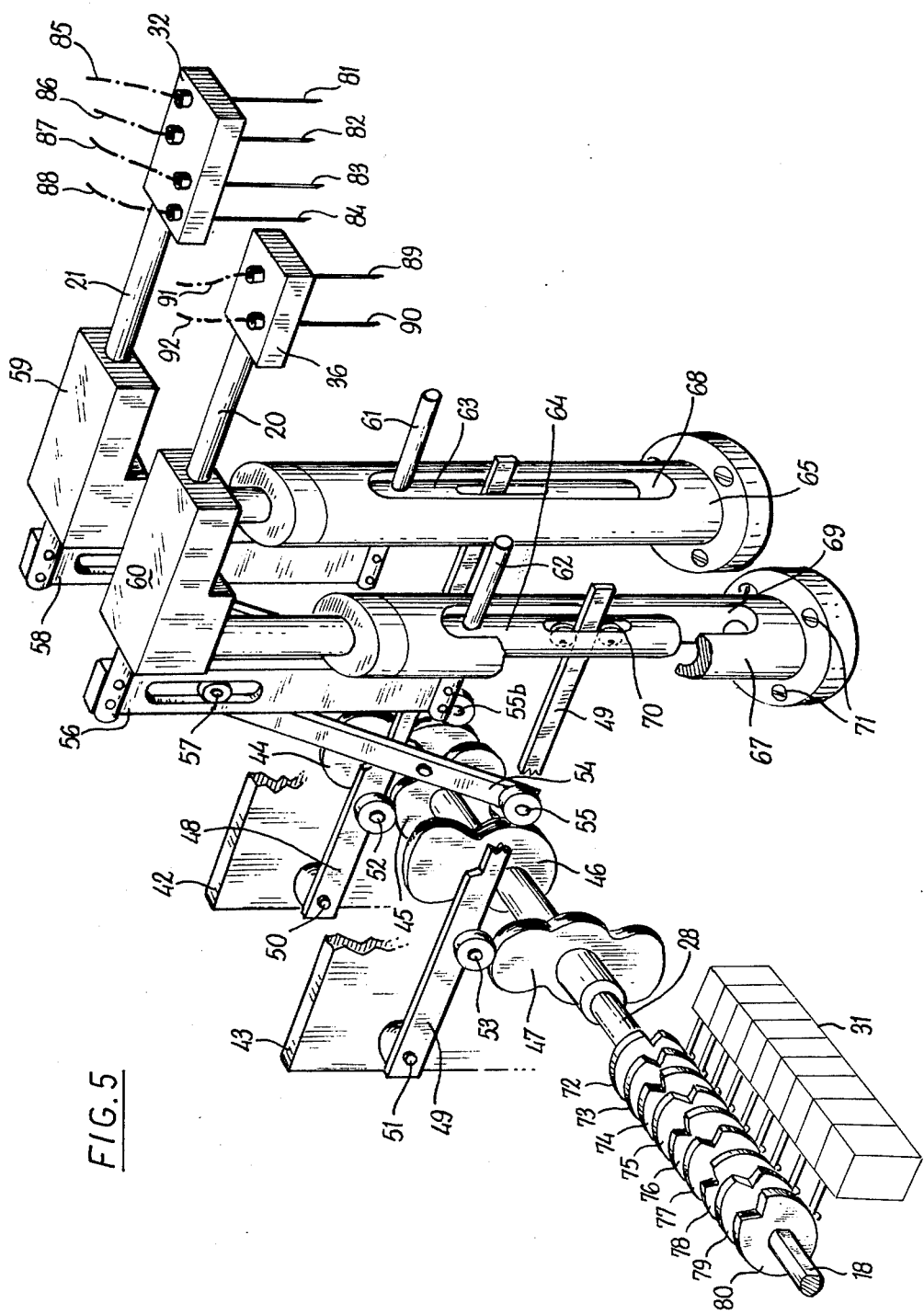
FIG. 5 shows the detail of the operating unit for the needle-carrying heads and of the associated arms, in perspective view and with certain parts in sectional view.

The FIG. 5 shows in detail the operating system for the arms 20 and 21. On two support plates 42 and 43 are mounted respectively the lever 48 for the vertical movement of the sampling arm and the lever 49 of the transfer arm, with the respective pivot pins 50 and 51.

On the shaft 28 are mounted four cams for the horizontal and vertical movements of the two arms. The cam 44 serves for the horizontal movement of the sampling arms 21 and has a three lobe shape for three horizontal movements. The cam 45 serves for the vertical movement of said arm 21. The cam 46 serves for the horizontal movement of the transfer arm 20. Said cam has two lobes for two horizontal movements of the arm. The cam 47, having a "butterfly" shape, imparts the vertical movement to the transfer arm 20. Four bearings 52, 53, 55 and 55B are used for the movements of said cams 44, 45, 46 and 47. The guides 56 and 58 serve for the horizontal movement of the arms 20 and 21, while the lever 54 serves for the horizontal displacement of the arm 20. The levers 48 and 49 are received within the slots 66 and 70 and serve for the vertical displacement of the arms 20 and 21. The guide rods 61 and 62 serve for the horizontal movement of the arms 20 and 21. Two support uprights 65 and 67 fixed to the base 15 by the screws 71 are inside provided with the guide slots 68 and 69 for the shafts 63 and 64. The arms 20 and 21 are slidingly mounted in the blocks 59 and 60 and terminate with the needle carrying heads 32 and 36. The needle carrier 32 contains four needles. Two needles 81 and 82 are connected to the pipes 85 and 86 for drawing the washing liquid and the sample to be analyzed. The needles 83 and 84 are connected to the pipes 87 and 88 for drawing and delivering the reagents. The needle carrier head 36 contains two needles 89 and 90 connected to the pipes 91 and 92 serving for the transfer of the liquid for the photometric metering and for the washing.

Still FIG. 5 shows the array of cams having the profiles 72 and 80 each of which is associated to a microswitch 31. Said cams serve to synchronize the various operative stages with the operation of the two needle carrying heads 32 and 36.

The functions of the various cams are as follows:
Cam 72—Sample drawing and washing control
Cam 73—Sample drawing control
Cam 74—Reagent drawing control
Cam 75—Liquid transfer control
Cam 76—Washing and drawing control of metering samples
Cam 77—Photometric read out control
Cam 78—Computer signal control
Cam 79—Automatic washing control
Cam 80—Automatic stop control.

The FIG. 6 shows the sequence of the operative stages of the two needle carrying heads 32 and 36.

When the head 32 with four needles is in position I, the needles 81 and 82 draw two amounts to be analyzed by a single sample-carrying capsule 94 and simultaneously the needles 83 and 84 deliver two reagents into two adjacent reaction test tubes 93. In position II the arm 21 moves upwards with all four needles and horizontally inwards in III, moving downwards in the position IV in order to deposit the sample and its washing into reaction test tubes 93. In the position V the arm moves again upwards and horizontally inwards and in position VI it moves downwards so that the needles 82 and 83 enter into the cup 33 containing the washing liquid of the sample and the needles 83 and 84 enter into the cups 34 which contain reagents.

The needle carrying head 36 is provided with the two needles 89 and 90 which in position I enter into the reaction test tubes 93 for drawing one or two solutions ready for read out in the photometer. In position II the needles will move upwards and horizontally inwards in the positions III, IV and V, in the position VI the needles enter into the cup 35 for drawing the washing liquid of the photometric cup.

The drawing of the liquid for metering by means of the needles 89 and 90 occurs through the drawing system 17. The drawing of the sample to be analized is carried out by means of the adjustable samplers 4 and is carried out by the needles 81 and 82. Also the washing of the sample drawn by the needles 81 and 82 is carried out by means of the double doser 19. The needles 83 and 84 will draw and deliver reagents by means of the double doser 25.

The present invention has been described in one preferred embodiment being however understood that constructive variants might be practically adopted without departing from the scope of the present industrial privilege.

Having thus described the present invention, what is claimed is:

1. A two-channel analyzer for the analysis of liquid samples comprising, in combination: a rotatable plate comprising and internal circular sample plate portion adapted to carry a single row of a number of oval shaped sample-containing cups and an external circular analytical plate portion adapted to carry two concentric and parallel rows of reaction test-tubes, said plate portions being radially aligned so that each sample-containing cup corresponds to and is radially aligned with two reaction test tubes; means to rotate stepwise said circular plate; a first moving-arm located above both said plate portions for aspirating two samples to be analyzed at one time from a single oval sample-cup and for transferring the aspirated samples including a wash-solution and respective reagents into two separate reaction test tubes to form a pair of solutions; and a second moving-arm located above said analytical plate portion for aspirating the solutions from two separate reaction test tubes and transferring the two solutions simultaneously for separate measurement at one time.

2. A two-channel analyzer as defined in claim 1 further comprising a support plate and wherein the circular plate consists of two circular plates divided into circular segments, wherein the inside plate comprises said sample plate portion and consists of one row of oval sample containing cups and the outside plate comprises said analytical plate portion and consists of two rows of concentric and radially aligned reaction test tubes, and wherein the circular segments are removably mounted on said support plate, so as to allow the quick substitution of groups of sample-containing cups and/or groups of its associated reaction test tubes for continuous operation or changing from one test to another.

3. A two-channel analyzer as defined in claim 1 in which said first movable arm is provided with two pairs of needles, where one pair of needles provides means for aspirating two micro-quantities of sample from a single sample-containing cup and transferring them together with a previously aspirated wash solution into two separate reaction test tubes, and wherein the second pair of needles provides means for aspirating two exact quantities of reagents and transfers them simultaneously into two adjacent reaction test tubes.

4. A two-channel analyzer as defined in claim 1 further comprising two measuring cells for measuring the solutions and wherein said second movable arm includes a single pair of needles for aspirating the solution for measurement from two separate reaction test tubes and transferring them to said cells for measurement, and for aspirating a wash-solution to rinse the two measuring cells between solutions.

5. A two-channel analyzer as defined in claim 1 in which the single sample-containing cups are shaped and disposed within said sample plate portion so as to allow the aspiration of two different samples simultaneously from a single sample-cup.

6. A two-channel analyzer as defined in claim 1 further comprising a support plate and wherein the sample-containing cups and its respective two rows of reaction test tubes are held on said support plate and rotatable together.

7. A two-channel analyzer as defined in claim 1 further comprising a computer and a double photometric measuring device coupled with said computer being adapted for processing data and providing control of all operating cycles of said analyzer and including a digital display and printout for displaying and printing out the results of two different tests simultaneously.

8. A two-channel analyzer as defined in claim 1 wherein said first arm includes a four needle carrying sampling head wherein said sampling head is arranged to effect horizontal and vertical displacements in three positions, wherein said second arm includes a transfer head, and wherein said transfer head is arranged to effect vertical and horizontal displacements in two positions.

9. A two-channel analyzer as defined in claim 1 further comprising a single shaft, a single motor, and a group of cam-controlled levers mounted on said single shaft and driven by said single motor for moving said arms and causing the stepwise rotation of said plate.

10. A two-channel analyzer as defined in claim 9 further comprising a second set of cams and a plurality of micro-switches, said second set of cams being mounted on said single shaft and associated with said micro-switches for controlling the complete synchronization and different operations of the system including the aspiration of the samples and its wash-solution, the aspiration and dispensing of reagents, the transfer of ready solutions for measurement, the wash between samples to avoid contaminations, and the read-out and print-out of the measurement results.

11. A two-channel analyzer as defined in claim 1 further comprising a plurality of needles carried by said first arm for aspirating the samples and means for washing said needles both internally and externally prior to said needles passing to the next sample to avoid carry-over by immersion in and aspiration of wash-solution.

12. A two-channel analyzer as defined in claim 1 further including a container including two compartments and a pair of needles carried by said first arm, said compartments being adapted for containing two different reagents necessary for two different tests, wherein said needles are adapted to immerse into the two compartments and to aspirate two different reagents for distribution.

13. A two-channel analyzer as defined in claim 1 further including a measuring cell for providing the measurements tests and a container adapted to hold wash-solution and located under the second arm, said container providing after each aspiration of sample for measurement, a wash-solution to rinse the measuring cell to avoid contamination from sample to sample.

14. A two-channel analyzer as defined in claim 1 further comprising a thermostatic block and wherein the reagents and the wash-solutions are immersed in said thermostatic block and distributed heated thereby to speed up reaction time of the samples and the reagents.

* * * * *